United States Patent
Haavig et al.

(10) Patent No.: US 6,639,672 B2
(45) Date of Patent: Oct. 28, 2003

(54) METHOD AND APPARATUS FOR RAPID PARTICLE IDENTIFICATION UTILIZING SCATTERED LIGHT HISTOGRAMS

(75) Inventors: David L. Haavig, Laguna Hills, CA (US); Gary Lorden, Pasadena, CA (US)

(73) Assignee: Micro Imaging Technology, Laguna Hills, CA (US)

( * ) Notice: Subject to any disclaimer, the term of this patent is extended or adjusted under 35 U.S.C. 154(b) by 0 days.

(21) Appl. No.: 10/197,639

(22) Filed: Jul. 15, 2002

(65) Prior Publication Data

US 2002/0186372 A1 Dec. 12, 2002

Related U.S. Application Data

(63) Continuation-in-part of application No. 09/501,840, filed on Feb. 10, 2000, now Pat. No. 6,421,121.

(51) Int. Cl.$^7$ .............................................. G01N 21/00
(52) U.S. Cl. ...................................... 356/338; 356/343
(58) Field of Search ................................. 356/335, 336, 356/337, 338, 343

(56) References Cited

U.S. PATENT DOCUMENTS

| | | | | |
|---|---|---|---|---|
| 4,735,504 A | * | 4/1988 | Tycko | 356/336 |
| 4,781,460 A | * | 11/1988 | Bott | 356/336 |
| 5,367,474 A | * | 11/1994 | Auer et al. | 702/21 |
| 5,760,900 A | * | 6/1998 | Ito et al. | 356/338 |
| 6,421,121 B1 | * | 7/2002 | Haavig et al. | 356/338 |

* cited by examiner

*Primary Examiner*—Michael P. Stafira
(74) *Attorney, Agent, or Firm*—Frank Frisenda

(57) ABSTRACT

Unique methods and apparatus are provided for rapidly identifying microscopic particles, such as protozoa and other microbes suspended in a fluid or gas. In one embodied form, the apparatus comprises: a polarized laser that produces a beam waist; an optical chassis including multiple light detectors, each light detector positioned around and oriented to view, without obscuration, a common region of regard of the laser beam waist; a sample chamber for containing a fluid sample to be analyzed; means for holding the sample chamber in a prescribed orientation with respect to the laser beam waist and in the common region of regard of the light detectors; means for causing the particles in the sample to circulate through the laser beam waist; means for covering the light source and optical chassis to create a dark enclosure; means for converting the light intensity values measured by the detectors into digital values; means for continuously entering the digital values into a computer; means for determining when a particle has entered the light beam at the common region of regard based on the digitized measurements; means for converting the digitized values to calibrated values; means for extracting Event Descriptors from the digitized and calibrated event data; means for calculating Discriminant Function values from the Event Descriptors; and means for defining probability histograms that enable the calculation of the probability that a Discriminant Function value calculated from measured values was caused by a specific particle species

7 Claims, 5 Drawing Sheets

METHOD AND APPARATUS FOR RAPID PARTICLE IDENTIFICATION UTILIZING SCATTERED LIGHT HISTOGRAMS

CROSS REFERENCE TO RELATED APPLICATION

This application is a continuation-in-part of our prior U.S. application Ser. No. 09/501,840, filed Feb. 10, 2000 projected U.S. Pat. No. 6,421,121 to be issued Jul. 16, 2002.

BACKGROUND OF THE INVENTION

The present invention provides unique methods and apparatus for identifying microscopic particles, such as protozoa and other microbes suspended in a fluid or gas.

Currently accepted methods for identification of pathogenic microscopic particles require relatively long, labor-intensive process. For instance, to determine whether *Cryptosporidium parvum* or *Giardia lamblia* is present in drinking water, suppliers must employ the USEPA method 1622, a long and labor-intensive procedure. Clinical laboratories and food inspectors also must use long labor-intensive procedures to locate and identify harmful bacteria.

Unfortunately, there are many circumstances when positive identification of a microbe cannot wait. A contamination of drinking water by Cryptosporidium must be recognized immediately, before the water is delivered to homes. Likewise, identification of a specific cause of a disease, such as bacterial meningitis, many times cannot wait the hours required. Finally, detection and identification of bacteria in food sources, such as beef, takes so long that in most cases, the food is distributed before the problem is discovered.

A variety of methods and apparatus exist for detection of microscopic organisms. For instance, De Leon, et al. in U.S. Pat. No. 5,770,368 teaches Cryptosporidium detection methods. The viability or infectivity of the encysted forms can be determined by synthesizing a cDNA from an induced HSP RNA template using a primer that is specific for particular genus or species of protozoa, followed by enzymatic amplification of cDNA. Alternatively, infectivity can be determined by amplifying HSP DNA from infected cells using a primer pair that is specific for a particular genus or species of protozoa.

Steele, et al. in U.S. Pat. No. 5,693,472 discloses detection of *Cryptosporidium parvum*. A method and kit for the detection of *Cryptosporidium parvum* in aquatic and biological samples such as surface water or feces is described. The method relies on the use of primers to detect all or a portion of at least one DNA sequence characteristic of *Cryptosporidium parvum,* the sequence being all or part of the genomic regions referred to as 38G and HemA contained within recombinant plasmids pINV38G, and pHem4, respectively.

Pleass, et al. in U.S. Pat. No. 5,229,849 discloses laser Doppler spectrometer for the statistical study of the behavior of microscopic organisms. An improved method and system of monitoring and identifying microbiota swimming in a fluid or moving across surfaces in a fluid provides a sensitive method for rapidly measuring very small changes in activity, and detecting and identifying individual microbes in relatively large volumes of fluid, even in the presence of detritus. The system comprises a laser station, a sample collector station, a picture taking station and a monitoring station.

Wyatt, et al. in U.S. Pat. No. 4,548,500 teaches process and apparatus for identifying or characterizing small particles. An apparatus and process are described for the characterization and/or identification of individual microparticles based upon the measurement of certain optical observables produced as each particle passes through a beam of light, or other electromagnetic radiation. A fine beam of, preferably, monochromatic, linearly polarized light passes through a spherical array of detectors, or fiber optics means, to transmit incident light to a set of detector means, and a stream of particles intersects the beam at the center of the spherical array. Selected observables calculated from the detected scattered radiation are then used to recall specific maps, from a computer memory means, one for each observable.

Lee, et al. in U.S. Pat. No. 5,473,428 disclose an interferometric temperature sensing system having a coupled laser diode wherein the magnitude is adjusted corresponding to a prior feedback laser beam. An interferometric temperature sensing system provides a simplified design for accurately processing an interference fringe pattern using self coupling effects of a laser detection element, where a laser diode and an optical detection element are combined in one package.

Curtis Thompson's U.S. Pat. No. 5,582,985 teaches detection of mycobacteria. The invention provides a method, compositions, and kits useful for detecting mycobacteria in a sample. The method includes contacting the sample with a formaldehyde solution, an organic solvent, and a protein-degrading agent prior to hybridizing a mycobacteria-specific nucleic acid probe to the sample. The invention has particular utility in detection and susceptibility screening of human-disease causing mycobacteria such as mycobacterium tuberculosis.

SUMMARY OF THE INVENTION

The unique system of the present invention provides accurate and valid measurements for identifying a wide variety of microscopic particles, such as protozoa and other microbes suspended in a fluid or gas. The inventive methodology provides a procedure for the quantitative and qualitative identification of particle species derived from measurement of light scattered by the particle that is collected by an array of optical sensors surrounding the suspended particle, in a convenient and reliable manner.

In more detail, the light scattered by the suspended particle is detected by the sensor array and converted to an electrical signal, e.g. a voltage. The voltage from each sensor is entered into a modifying means component where the voltages are digitized and the resulting values are used as fingerprints for particle identification. The unique modifying component comprises prediction formulas derived from one or more sets of empirically determined one-dimensional or multi-dimensional probability histograms that are functions of one or more mathematical combinations of the digitized voltages. Each set consists of individual probability histograms, which give the likelihood that observed values of specific combinations of digitized voltages were produced by a specific particle species. Thus, the unique modifying component of the inventive system interprets the measured signals as "species specific" when the prediction formulas result in probability values that are large for a specific species.

In one embodied form, the inventive method for rapidly detecting and identifying microscopic particles for quantitative and qualitative measurement comprises the steps of:

a) suspending the particle to be identified in a control fluid contained within a sample chamber;

b) holding the sample chamber in a prescribed orientation with respect to an intense light source;
c) illuminating the sample chamber with said light source;
d) collecting and measuring the scattered light from the sample chamber by means of an array of optical sensors surrounding the sample chamber;
e) converting a voltage output from the array of sensors to a digital signal as the particle passes through the intense light source; and
f) comparing the derived signal with a library of probability histograms and statistically classifying the resultant data to identify the microscopic particles present.

In accordance with the present invention, the library consists of histograms for each particle species encompassed by a statistical classification algorithm that calculates the probabilities that the associated signal was produced by those particle species. The probability histogram is derived empirically from a measure of the frequency that a species of microparticle is associated with a specific range of values of a mathematical combination of the digitized sensor voltages. Thus, the frequency-of-occurrence histogram can be produced for one mathematical combination, i.e., a one-dimensional analysis or alternatively, can be produced for multiple mathematical combinations simultaneously, i.e., a multi-dimensional analysis.

In a presently preferred embodied form, the inventive apparatus comprises, in combination:

a) a polarized laser that produces a beam waist;
b) an optical chassis including multiple light detectors, each light detector positioned around and oriented to view, without obscuration, a common region of regard of the laser beam waist;
c) a sample chamber for containing a fluid sample to be analyzed;
d) means for holding the sample chamber in a prescribed orientation with respect to the laser beam waist and in the common region of regard of the light detectors;
e) means for causing the particles in the sample to circulate through the laser beam waist;
f) means for covering the light source and optical chassis to create a dark enclosure;
g) means for converting the light intensity values measured by the detectors into digital values;
h) means for continuously entering the digital values into a computer;
i) means for determining when a particle has entered the light beam at the common region of regard based on the digitized measurements;
j) means for converting the digitized values to calibrated values;
k) means for extracting Event Descriptors from the digitized and calibrated event data;
l) means for calculating Discriminant Function values from the Event Descriptors;
m) means for defining probability histograms that enable the calculation of the probability that a Discriminant Function value calculated from measured values was caused by a specific particle species;
n) means for identifying the most effective Discriminant Functions.
o) means for storing the probability histograms and Discriminant Functions in an Identification Library, one histogram for each particle species that can be identified and each Discriminant Function;
p) means for retrieving previously stored probability histograms and Discriminant Functions, one probability histogram for each particle species that can be identified with the Identification Library and each Discriminant Function;
q) means for calculating the probability for each particle species in the library for a given value of a Discriminant Function;
r) means for combining probabilities for each particle species that can be identified with the Identification Library; and
s) means for identifying the unknown particle based on a threshold.

DETAILED DESCRIPTION OF THE PREFERRED EMBODIMENTS

Figure 1:
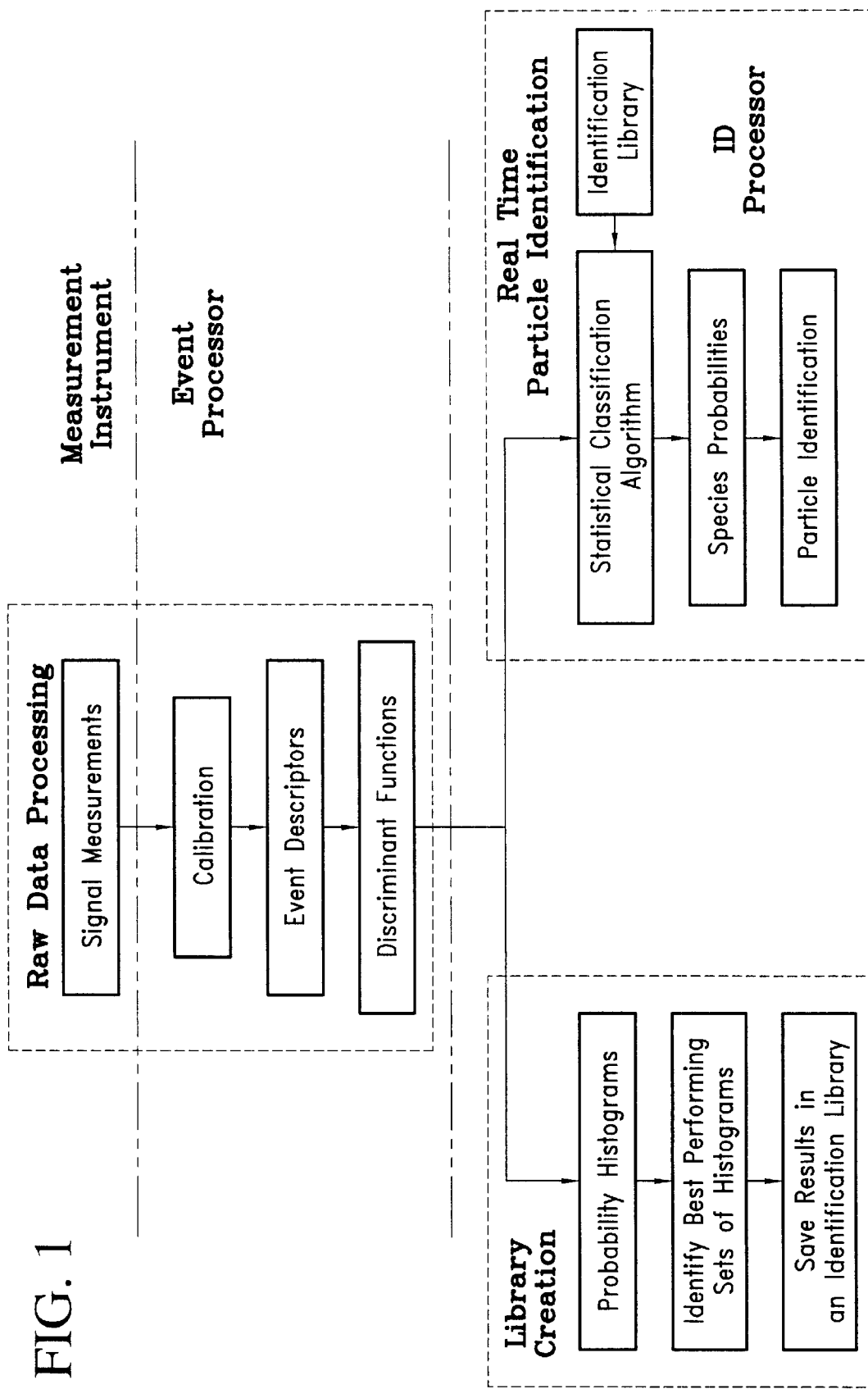
FIG. 1 is a flow chart showing the steps to create an Identification Library and to identify particles using the Identification Library using the preferred embodied form of this invention.

The present invention provides a unique method and apparatus for a microscopic particle identification method based on a statistical analysis of measured data. The method depends on three interrelated parts (see FIG. 1): The measurement instrument and raw data processing system; the creation of an Identification Library; and the use of the Identification Library.

This invention provides the means to rapidly detect and identify microbes and other types of particles. The system is based on a measure and analysis of light scattered off particles as they pass through an intense collimated light source. When particles are comparable to and somewhat larger than the wavelength of the incident light, light predominantly diffracts off the particle, scattering light energy in all directions. The light intensity in the various directions depends explicitly on the size and shape of the particle and wavelength of the incident light. In principle, one may calculate a particle size and shape from a high angular resolution measure of the light intensity and electromagnetic phase of all the scattered radiation. This, in fact, is a common practice in aerospace when dealing with radar signatures of vehicles. However, this technique is impractical when dealing with visible light. Additionally, measuring the exact size and shape of particles, such as bacteria, is not useful for identification due to natural size and shape variations. In accordance with the present invention, a system for particle identification by measuring only a small part of the scattered light is provided. By comparing the measured result with a library of previously made measurements, performed on a variety of types of particles, accurate particle identification is achieved.

The following definitions will be helpful to create a more complete description of the preferred embodiments.

The term "fluid" shall mean a liquid or gas media.

The term "light" shall mean electromagnetic radiation.

The term "common region of regard" shall mean a small region in space that is viewed simultaneously by all light detectors.

The term "without obscuration" shall mean no visual blocking, warping or vignetting.

The term "transparent" shall mean optically clear at the wavelength of employed light.

The term "sample chamber" shall mean a transparent enclosure that contains the sample.

The term "detectors" shall mean an electronic device that is sensitive to light and converts the incident light into a voltage or current with magnitude proportional to the incident light intensity.

The term "optical chassis" shall mean the framework, optical detectors and electronics that surround the sample chamber.

The term "apply calibration" shall mean to make corrections to the raw measured data such that measurements of standards will result in correct values.

The term "particle species" shall mean an individual class of particle such as a species of a microorganism or pollen or the type of article such as red blood cell, etc.

The term "event" shall mean a set of measured scattered light data taken as one particle passes through the light beam.

The term "frequency-of-occurrence histogram" shall mean a measure of how often the measurement of a particle species results in a specific value range for a given calculation of a mathematical combination of specific measurements.

The term "probability histogram" shall mean a normalized frequency-of-occurrence histogram such that the area under the curve (one-dimensional case) or the volume under the curve (multi-dimensional case) is one.

Figure 2:
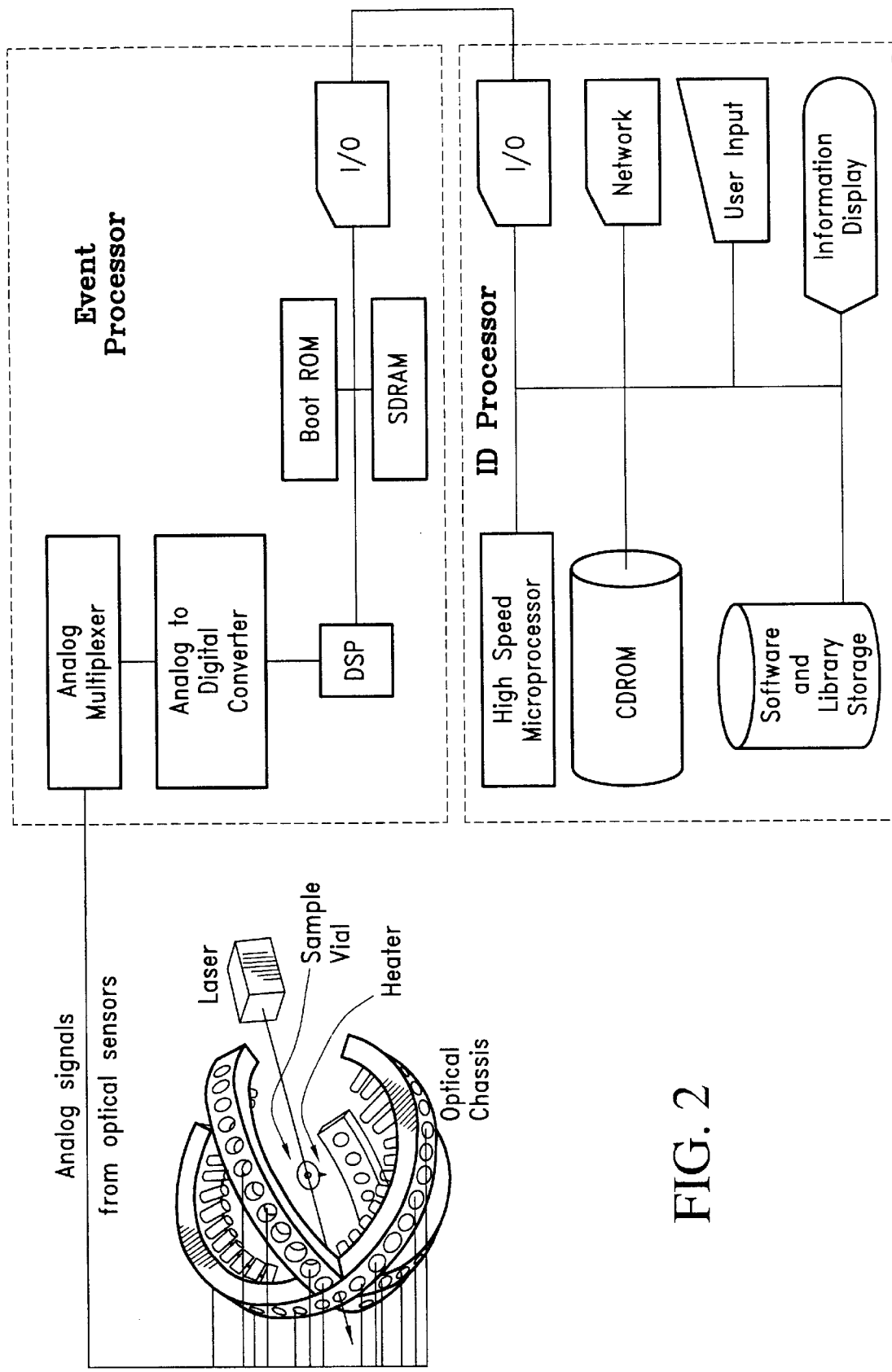
FIG. 2 is a schematic of the complete identification system.

In one embodied form, the inventive method for rapidly detecting and identifying microscopic particles for quantitative and qualitative measurement (the third of three inter-related parts) uses the measurement instrument shown in FIG. 2 and comprises the steps of:

a) suspending the particle to be identified in a particle free water contained within a glass vial;

b) holding the sample vial in an intense laser source such that the beam waist passes through the center;

c) collecting and measuring the scattered light from the glass vial by means of an array of optical sensors surrounding the sample chamber;

d) converting a voltage output from the array of sensors to a digital signal as the particle passes through the intense light source; and e) comparing the derived signal to at least one set of probability histograms to identify the microscopic particles present.

Accordingly, the identification of a particle species proceeds by initially measuring a statistically significant number of that species and deducing pertinent information from the measurements. After the collecting and archiving the relevant information in an Identification Library, identification of unknown particles proceeds by comparison of new measurements with the archived library of particle characteristics.

The system utilizes light scattered off particles that pass through the intense light source. FIG. 2 shows a schematic of one embodied form of an instrument to measure the scattered light and perform library creation and particle identification. An Optical Chassis provides the framework to support the optical detectors and constrain their field-of-view to a single common region of regard. The optical detectors collect and measure the intensity of the light scattered outside a sample chamber. An Event Processor subsystem continuously digitizes the voltage generated by the detectors and monitors the digitized voltage to dynamically extract a background signal and to determine when a particle passes through the laser beam.

When the Event Processor detects a particle passing through the laser beam, the processor keeps the digitized voltage from each detector until the particle passes completely through the beam. After the particle passes through the beam, the Event Processor applies calibration, then extracts from the digitized data, specific data (Event Descriptors) required by the particle identification algorithm and passes the Descriptors to the ID processor subsystem.

The ID Processor subsystem uses the Event Descriptors to form Discriminant Function values to cross-reference into the particle species Identification Library. The library contains numerous sets of probability histograms that can be used to calculate the probability that observed Discriminant Function values resulted from specific particle species. The ID Processor uses the probability histograms and a statistical classification algorithm to deduce the identity of the particle that passed through the laser beam. The ID Processor presents the identity of the particle on the display.

Thus, the first inventive process stage creates the Identification Library utilizing a large number of measurements by the measurement instrument. The second inventive process stage uses the measurement instrument and library to identify unknown particles.

Figure 3:
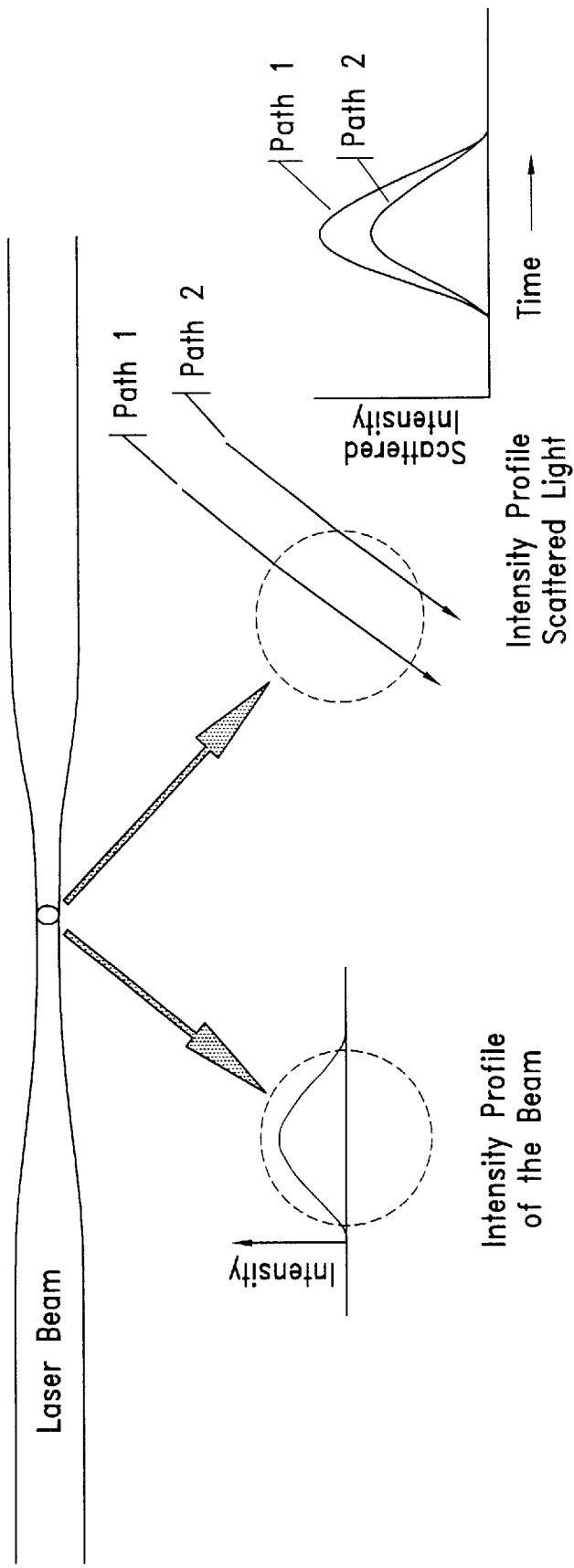
FIG. 3 is a close up of the beam waist of the laser. If the laser has a Gaussian intensity profile, spherical particles passing through the laser beam will scatter light that has a Gaussian shape versus time.

Understanding the Library creation process relies on understanding data measured for a spherical particle. When a spherical particle passes through the collimated beam, the photodetectors measure a time dependent intensity dependent on both the particle speed and the cross-sectional intensity profile of the laser. FIG. 3 shows that when the laser has a Gaussian cross-sectional intensity profile, a spherical particle will also have a Gaussian scattered light intensity versus time (note: the particle is much smaller than the diameter of the beam). Thus, v(d,t), the voltage measured on detector, d, as a function of time, t, is also Gaussian. The same particle passing through the beam waist along different paths will show Gaussian profiles with different magnitudes. Dividing the measured values, at each instant in time, by a sum of one or more of the detector values at the same instant in time removes this path dependency. Thus:

$$v'(d,t) = v(d,t)/\Sigma_{d'} v(d',t).  \quad \text{Equation (1)}$$

Here, d' is some or all of the detectors. When the particles are spherical, the normalized values, v'(d,t), are constant as long as the signal strength is large enough. Additionally, the value is independent of the path taken by the particle as it passes through the laser beam.

The value of the ratio for spherical particles from equation (1) is predictable when the wavelength, particle diameter and the index-of-refraction of the particle and the fluid are known. Thus, for spherical particles, it is sufficient to use a single ratioed value from each detector to characterize the particle that passed through the beam. These single ratioed values from each detector are called Event Descriptors since they uniquely describe the source of the event, that is, the particle that caused the event. In the following, ED(d) shall represent the Event Descriptor for detector d, that is, ED(d)= v'(d,$t_1$) where $t_1$ is a specific instant in time. Every spherical particle with the same size will produce the same Event Descriptors, ED(d). Thus, given a measurement of a spherical particle event, the diameter of the particle can be derived, in principle, from the values of the event descriptors.

When the particle is not a sphere, the Event Descriptors of equation (1) are no longer constant. A plot of v'(d,t) versus time will not result in straight lines. The shape of the curve depends on the orientation of the particle as it passes through the beam. The same particle passing through the laser beam repeatedly will produce a variety of plot shapes. Likewise, different particles of the same particle species will also produce a variety of plot shapes. As a result, the Event Descriptors as described above depend on time. Consequently, to account for non-spherical particles, the concept of the Event Descriptor is relaxed to denote data that simply is characteristic of the event even though the descriptor value may not be constant in time for the particle species.

The identification method requires a specific scheme to extract Event Descriptors from the event data. There are a variety of schemes. Two are:

1. Select an Event Descriptor value that is the maximum value of ED(d,t)=v'(d,t) attained during the event. That is:

$$ED_d = \max(v(d,t)/\Sigma_{d'} v(d',t)).$$

2. Select an Event Descriptor value that is the value of ED(d,$t_n$)=v'(d,$t_n$) at the time, $t_n$, when the value v'($d_n$,t) is a maximum for a specific detector, $d_n$, during the event. That is: $ED_d = v(d,t'_n)/\Sigma_{d'} v(d',t'_n)$ where $t'_n$ is the time when detector d=n is a maximum.

Since the event data measured when a non-spherical particle passes through the laser beam depends on its orientation, one cannot directly identify the particle given the Event Descriptor values. However, one can use a statistical analysis to predict what the particle was. Measuring many particles of the same species will produce a family of Event Descriptor values. The family of values describes the range of values that the Event Descriptors take. It is important to note that the range of values is limited in extent. Plotting these measured values as a frequency-of-occurrence histogram versus Event Descriptor value results in a graph similar to that in FIG. 4. As this graph indicates, the range of values for Event Descriptors are limited and, more importantly, some values are more likely than others are.

Figure 4:
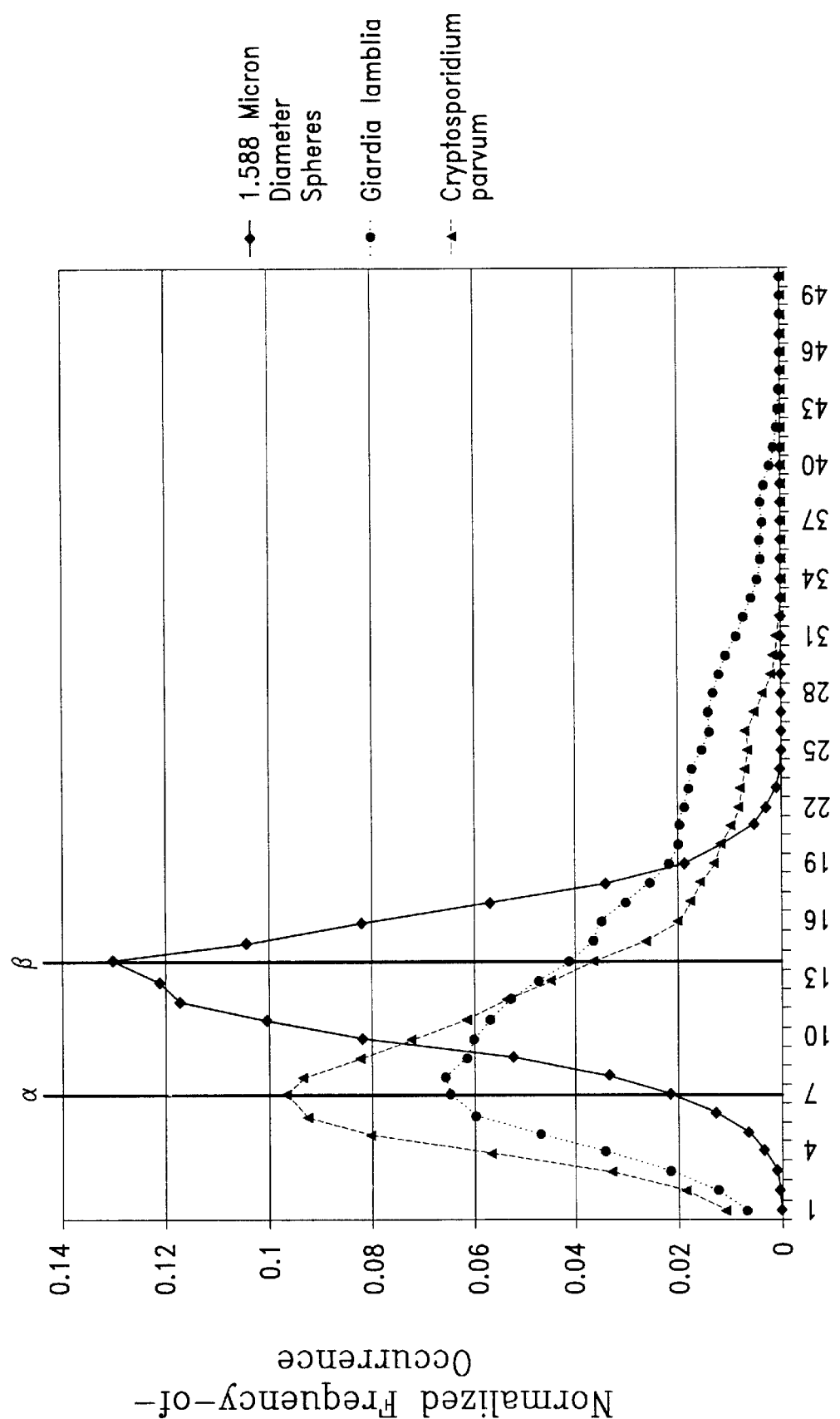
FIG. 4 shows three normalized frequency-of-occurrence histograms. These plots show results for measured data of three particle species: a sample of 1.588±0.025-micrometer diameter polystyrene spheres (standard deviation of 0.016 micrometer), *Giardia lamblia* and *Cryptosporidium parvum*.

A frequency-of-occurrence histogram plot for a different particle species will result in a somewhat different histogram graph since the particles will have different size, shape or optical characteristics. FIG. 4 shows normalized histogram plots for three different particle species: *Giardia lamblia*, *Cryptosporidium parvum* and a sample of 1.588 micrometer diameter polystyrene spheres for an Event Descriptor, $ED_1$. Given a specific measured value for $ED_1$, such as the point α on the graph, one can deduce that the particle is likely to be a *Giardia lamblia* or Cryptosporidium. Likewise, if the value is β, then the particle is likely to be a 1.588-micrometer diameter sphere. However, the identification is not absolute. At both point's α and β, there is still a non-zero chance that the event was caused by any one of three particle species.

Clearly, the process requires additional information to increase the likelihood of an accurate identification. The additional information comes from using another set of histograms for a different Event Descriptor, $ED_2$ and so on. The identification process becomes a matter of deducing a particle species from the probability that measured Event Descriptor values were produced by the different particles in the data set of pre-measured histogram curves. The data set of pre-measured normalized histograms is called an Identification Library.

The Library Creation stage starts with the Event Descriptors extracted from the event data and processed by the measurement instrument. The Event Descriptors are reorganized into a large set of Discriminant Functions. Probability histograms for each function and each different particle species to be included in the library are calculated. The strength of each Discriminant Function in providing species-to-species distinction is calculated. The best Discriminant Functions are identified and pertinent data saved for use by the identification procedure.

Discriminant Functions enhance the distinction between particle species. Consider data for two different spherical diameters. One finds cases where the value $ED_1$ is large for one sphere and small for the other sphere while $ED_2$ is small for the first sphere and large for the second. In this case, the ratio $ED_1/ED_2$ is a good discriminator between the two different spheres. This ratio is large for one sphere diameter and small for the other. In this case, a histogram for the values resulting from the Discriminant Function DF=$ED_1$/$ED_2$ will show greater separation between the curves for the two different particle species than the histograms of the individual Event Descriptors.

Discriminant Functions are simply generalizations of the Event Descriptor concept. For example, the following three relations between Event Descriptors are each Discriminant Functions: $DF_1=ED_1$, $DF_2=1/ED_2$ and $DF_3=ED_1/ED_2$. Since the Discriminant Functions include the individual Event Descriptors, the following discussion will only use Discriminant Function.

The histograms are easier to use when normalized. That is, the area under the curve is one (one-dimensional case) or the volume under the curve is one (multi-dimensional case). The resulting curves then are like probability densities. These probability histograms now give directly the probability that a specific Discriminant Function value resulted from a measurement of a specific particle species.

As described above, one probability histogram for each particle species cannot classify a measured Event as a specific particle species. Consequently, a set of densities derived from a set of Discriminant Functions is required. Unfortunately, there may exist Discriminant Functions that do not exhibit good separation between the probability histogram curves for different particle species as demonstrated in FIG. 4. While the separation between Giardia and the spheres and between Cryptosporidium and the spheres is good, the separation between Giardia and Cryptosporidium is not very good. Consequently, the Discriminant Function plotted in FIG. 4 does not provide useful identification information distinction between Giardia and Cryptosporidium. The choice of which set of Discriminant Functions to use for identification is crucial: Discriminant Functions cannot be chosen haphazardly. Additionally, there is no a priori reason to select one set of Discriminant Functions over another. Fortunately, given the high speed and large data handling capabilities of modern computers, one can simply calculate the densities for a large set of functions, sort through the results and identify those that provide good separation between the probability histogram curves for individual particle species.

With the best performing set of Discriminant Functions identified, the Identification Library may be created and archived. The Library must contain a list of the species encompassed by the probability histograms. Each set of probability histograms must have its associated Discriminant Function.

To identify unknown particles with the Identification Library, load the library into the identification computer memory. The measurement instrument and raw data analysis procedure measures the unknown particle and extracts Event Descriptor data as described.

The identification procedure begins by measuring and collecting the data for an unknown particle as it passes through the laser beam. The Event Processor digitizes the resulting signals and extracts the Event Descriptor data from the event. The Event Processor then passes the Event Descriptor data to the ID Processor that attempts to identify the particle.

The ID Processor begins by calculating values for the Discriminant Functions from the Event Descriptors for the first set of probability histograms in the library. Looking up or interpolating the probability values from the probability histogram for each respective particle species and applying a statistical classification algorithm determines the probability that a specific particle species generated these Discriminant Function values. The result is an array of probabilities associated with these first Discriminant Functions: p(df, species), where df in this case is the Discriminant Function set number, 1 in this case—that is, it is the first set of Discriminant Functions. The ID Processor repeats this process for all sets of Discriminant Functions and their associated probability histograms in the library.

One possible statistical classification algorithm uses the set of probability values described as p(df, species), where df is the specific Discriminant Function and species is the particle species, in the following way. The probabilities for each different particle species (species) are combined to form a single probability value for that species:

$$p(\text{species}) = \Sigma_{df} W(df) \times p(df, \text{species}),$$

where W(df) is a weighting for the probability histogram resulting from the Discriminant Function set, df.

Particle species identification occurs by proper interpretation of these final probability values. One embodied interpretation is to use thresholds. If p(species)>t(species), where t(species) is the threshold value for a specific particle species, and all other values are less than their thresholds, then the particle is identified as that species. If more than one probability is above its respective threshold or if no probabilities are above threshold then the particle cannot be identified.

In a presently preferred embodied form, the inventive apparatus comprises, in combination:

a) a polarized laser that produces a beam waist;
b) an optical chassis including multiple light detectors, each light detector positioned around and oriented to view, without obscuration, a common region of regard of the laser beam waist;
c) a sample chamber for containing a fluid sample to be analyzed;
d) means for holding the sample chamber in a prescribed orientation with respect to the laser beam waist and in the common region of regard of the light detectors;
e) means for causing the particles in the sample to circulate through the laser beam waist;
f) means for covering the light source and optical chassis to create a dark enclosure;
g) means for converting the light intensity values measured by the detectors into digital values;
h) means for continuously entering the digital values into a computer;
i) means for determining when a particle has entered the light beam at the common region of regard based on the digitized measurements;
j) means for converting the digitized values to calibrated values;
k) means for extracting Event Descriptors from the digitized and calibrated event data;
l) means for calculating Discriminant Function values from the Event Descriptors;
m) means for defining probability histograms that enable the calculation of the probability that a Discriminant Function value calculated from measured values was caused by a specific particle species;
n) means for identifying the most effective Discriminant Functions.
o) means for storing the probability histograms and Discriminant Functions in an Identification Library, one histogram for each particle species that can be identified and each Discriminant Function;
p) means for retrieving previously stored probability histograms and Discriminant Functions, one probability histogram for each particle species that can be identified with the Identification Library and each Discriminant Function;
q) means for calculating the probability for each particle species in the library for a given value of a Discriminant Function;
r) means for combining probabilities for each particle species that can be identified with the Identification Library; and
s) means for identifying the unknown particle based on a threshold.

The measurement instrument described above measures light scattered anywhere into the spherical region surrounding the scattering particle. This type of instrument is called a 3D instrument. A simplified variation of this instrument is a 2D instrument that measures light scattered only in a plane.

Further aspects of the present invention will be understood by reference to the following illustrative examples.

EXAMPLE 1

One embodied form of a 2D Instrument. The basic geometry of the system may be used, including the positions of the detectors. The detector electronics, digitizer subsystem, computer system, data collection software, and data analysis software are set forth in accordance with the present invention.

Fifteen detectors are mounted around a one-inch thick ring about 2.75 inches in outer diameter. The detectors are faced to view the center of that ring. Each detector views the ring center through a hole in the ring. This hole limits the field-of-view of the detector to about 0.1" at the ring center. The hole is tapped and black anodized to reduce sensitivity to light scattered within the hole.

A Helium-Neon laser emitting a polarized Gaussian beam at wavelength of 632.8 nanometers or a solid-state laser emitting a polarized Gaussian beam at wavelength of 660 nanometers is used as the light source. Either laser is mounted so that the beam passes through the ring center. The Helium-Neon laser beam is vertically polarized while the solid-state laser is horizontally polarized.

A cylindrical vial is used to contain the sample that is tested and measured. The vial is a colorless glass such as flint or borosilicate glass or colorless plastic such as polystyrene or polycarbonate. The vials have no visible imperfections such as scratches or ripples on the cylindrical side. The vial is mounted concentric with the ring and roughly centered along the cylindrical axis and supported from the bottom.

The ring, the detectors, the laser, and the buffer amplifiers are mounted within a light tight, electrically conductive enclosure. The enclosure may be mounted on vibration dampening material such as Sorbothane.

EXAMPLE 2

One embodied form of a 3D instrument comprises five arcs roughly eight inches in diameter and one inch thick. Two arcs are mounted concentrically on the same plane. Two other arcs are also mounted concentrically on the same plane. The two planes of these two pairs of arcs are mounted at 90 degrees from each other such that the center of curvature of all four arcs is at the same point. The two planes form an "X" when viewed looking along the intersection of the two planes. The fifth arc is mounted concentric with the other arcs and is oriented vertically on the bottom of the "X". Consequently, the fifth arc makes a 45-degree angle with the two planes.

A total of 37 detectors are mounted in the arcs. Eight detectors are mounted on each of the four arcs that make up the "X". Five detectors are mounted on the fifth arc. The detectors are positioned 15 degrees apart on the arcs starting 15 degrees from one end of the art, the same end for all arcs. The fifth arc has no detector at 15, 30, and 90 degrees.

The detectors are faced to view the center of curvature of the arcs. Each detector views the arc center through a hole in the arc. This hole limits the field-of-view of the detector to about 0.1" at the arc center. The hole is tapped and black anodized to reduce sensitivity to light scattered within the hole.

A solid-state laser emitting a polarized Gaussian beam at a wavelength of 660 nanometers is used as the light source. The laser is mounted so that the laser beam passes through the intersection of the two arc planes and consequently through the center of curvature of all the arcs. The laser is horizontally polarized.

Figure 5:
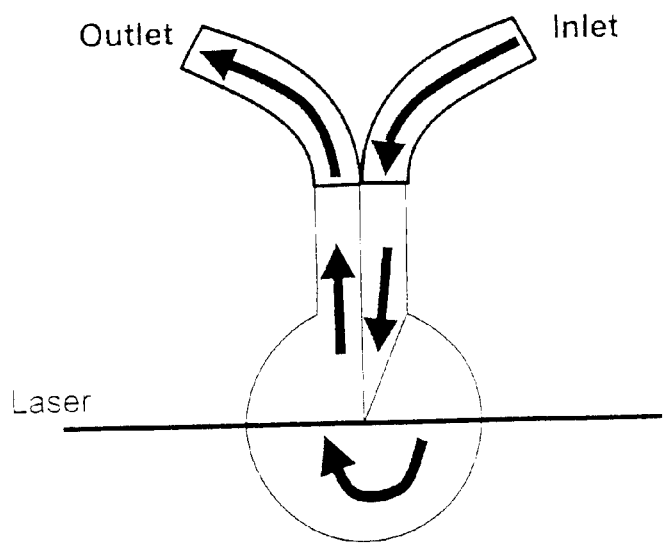
FIG. 5 is a schematic cross-sectional front view of one embodied flow vial design in accordance with the present invention.

A round bottom vial (see FIG. 5) is used to contain the sample being tested and measured. The vial is a colorless glass such as flint or borosilicate glass or a colorless plastic such as polystyrene or polycarbonate. The vials have no visible imperfections such as scratches or ripples on the spherical sides. The vial is mounted concentric with the arcs.

A variation of the round bottom vial is a round vial with two flat areas on opposite sides. This vial is positioned such that the laser light enters the vial through one flat area and exits through the second area. An additional extension of this vial concepts is to slant the flat area so that the reflected laser beam can be directed out of the way.

The voltage output from each detector is passed to a buffer amplifier board. The buffered signal from the buffer amplifier board is passed to a voltage digitizer. The digitized signal is either archived to a computer disk or analyzed in real time.

The arcs, the detectors, and the laser is mounted on vibration dampening materials such as Sorbothane. The arc, detector, and laser assembly as well as the vibration dampening materials and the buffer amplifier are mounted within a light tight, electrically conductive enclosure.

Measurement Process

Software is used to control the data collection process. First, the operator selects the various parameters that define how the data is collected. The parameters are:

1. The instrument configuration (the 2D or 3D instrument) being used.
2. The triggering scheme to be used for collecting data.
3. The operator (who is collecting the data).
4. The details of the sample being measured.
5. The duration of the measurement.
6. The time duration that is considered too long for a particle to be in the laser beam.

When all is selected, the operator initiates data collection. The data collection parameters are archived in a database. The software then continuously collects the digitized voltage from each detector on the instrument.

Triggering Schemes

The software monitors the voltage of the detectors specified by the selected triggering scheme to identify the presence of a particle in the laser beam, an event. We have implemented two different triggering schemes. The first is a simple thresholding scheme: a particle is declared as present then the voltage of the specified detector is above a threshold.

The second is a more complicated "dynamic thresholding" scheme. The background voltage (the signal when no particle is present) is continuously measured to allow for drift. The threshold used is specified as a multiple of the detector noise. Thus, low noise detectors can have a lower threshold than higher noise detectors. Additionally, more than one detector can be used as a trigger: the operator can select a group of detectors as trigger detectors and specify how may of those detectors must be triggered to declare the presence of a particle. Finally, the operator can select more than one group of trigger detectors wherein all groups must trigger to declare the presence of a particle.

When the presence of a particle is detected, the software looks for the end of the event using the same triggering scheme. The measured data then is written to disk and an entry added to the database. The data written includes measured data from all detectors measured from an operator-selected time before the initial trigger (the pre-trigger time) through an operator-selected time after the final trigger (the post trigger time).

The measurement process continues until the operator-selected measurement time has elapsed.

Calibration

NIST traceable size standards are used for calibration. The standards are spheres that are available in a variety of materials such as polystyrene and silicone dioxide and a variety of diameters. The tight constraint on both the certified mean diameter and its standard deviation allow a direct comparison between a measurement of these spheres on our instrument and that predicted by a MIE light scattering prediction for our instrument.

Calibration requires the measurement of a number of spheres with the same nominal diameter. Calibration factors are calculated to make the average of the measured values conform to those predicted by MIE light scattering. The resulting calibration factors are then used to correct all measured data for any instrumental variation.

The normal sample preparation procedure includes adding some spheres to the sample vial. Consequently, some of the events measured are spheres. The spheres allow a measurement-by-measurement calculation of calibration factors.

Particle Density Estimation

Calibration sphere measurements are very easy to discriminate from non-spherical particles. The scattered light intensity as a function of time always reflects the intensity profile of the laser. The lasers used have a Gaussian (or normal curve) shape. Measurements of spheres always result in a Gaussian shape. This easily determinable shape makes it simple to identify and count the spheres.

By adding a known number of calibration spheres to the sample vial, the number of other particles can be estimated by comparing count rates of the different particles.

Library Creation

The identification process uses two different types of libraries: Indication Libraries and Identification Libraries. An Indication Library looks at the measured event data and simply determines whether the event could be a specific particle species. An Identification Library looks at the measured event data and attempts to identify the particle species. Currently, each Identification Library can judge between a pair of particle species. To identify more than two particle species, additional Identification Libraries are required.

Figure 6:
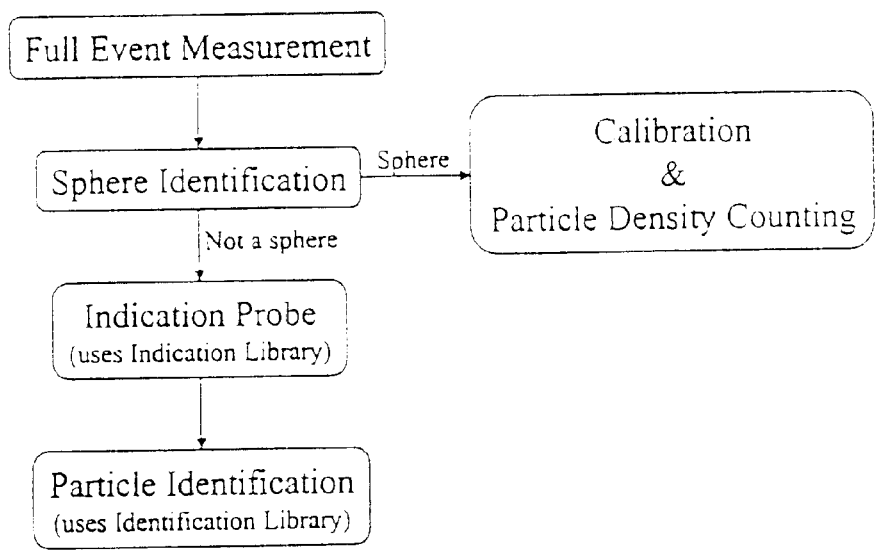
FIG. 6 is a diagram of one embodied particle identification method utilizing two different types of libraries (Assessment Libraries and Identification Libraries) in accordance with the present invention.

FIG. 6 diagrams the identification process. First, a measurement of an unknown particle is tested to determine if the particle is a sphere. If it is a sphere, then its measurement is used to derive calibration factors and counted. If the particle is not a sphere, the event undergoes an Indication Probe that determines what kind of particle species the event could be. Finally, only those particle species that were selected by the Indication Probe are tested by the Identification Libraries.

For example, if the Indiction Probe indicated that the event could be particle species "A," "B," and "C," then the event undergoes testing by the "A–B (that is A versus B)," "A–C," and "B–C" Identification Libraries.

Both Indicative and Identification Libraries are based on frequency-of-occurrence histograms as described in the patent document. An Indication Library uses normalized histograms. An Identification Library uses histograms with a little more processing. In each case, the resulting distribution is called a Likelihood Fingerprint.

Calculation of Frequency-of-Occurrence Histograms

The frequency-of-occurrence histograms are derived from archived measurements described above. The procedure is as follows:

1. Derive calibration. A file of raw measurements is scanned for spheres. Calibration factors are derived from the spheres in the file. From this point on, all data taken from the file have the calibration applied.
2. Extract Event Descriptions. Extract values from the each event that is characteristic of the event. During this step, the quality of each non-sphere event is ascertained. Every event must meet minimum quality requirements before it can be used in library creation. These requirements are:
   a. The event duration must be shorter than an experimentally determined time. Events longer than this time are almost always multiple events—more than one particle in the beam at a time. This time is easy to determine and eventually will be automatically determined.
   b. The event must be well delineated. The event must be well isolated from other events such that the detector signal strength is low before and after the particle enters the laser beam.
   c. The detector signal strength must be large enough on most detectors. Most particles do not pass through the laser beam center where the laser is most intense. Consequently, the signal we get varies considerably and we reject events that pass through the perimeter of the laser beam due to low signal.

The calibred signal from each detector is scanned to find its time of maximum signal. The calibrated signal from all detectors is taken at that instant in time. The end result is a 37×37 array of values for each event. This 37×37 array is archived on disk.

3. Histogram Calculation. There are a large number of different frequency-of-occurrence histograms that could be calculated. We currently use two-dimensional histograms. Each axis is a Discriminant Function value. The Discriminant Functions we use are simple ratios of Event Descriptor values taken from the same detector maximum time. Thus, one frequency-of-occurrence histogram could be a histogram of values derived from detector one divided by detector two on the x-axis versus detector three divided by detector four on the y-axis at a time defined by when detector five is a maximum.

Once the Discriminant Functions and the maximum detector have been chosen, frequency-of-occurrence histograms are calculated from extracted Event Descriptor data using this procedure:

a. One half of the Event Descriptor data is randomly selected.
b. The values of the two Discriminant Function values are calculated for each selected Event Descriptor value.
c. The values for the x-axis Discriminant Function are sorted.
d. The 0.5 and 99.5 percentile values are found. These two values set an initial minimum and maximum for the x-axis.
e. The values for the y-axis Discriminant Function are sorted.
f. The 0.5 and 99.5 percentile values are found. These two values set an initial minimum and maximum or the y-axis.
g. Next, a two-dimensional histogram using a 50×50 grid is created using the minimum and maximum values for each axis.
h. The resulting two-dimensional histogram is probed to determine its size on the 50×50 grid as well as the number of events in the cell with the most events. Size scale of the grid is adjusted and the histogram redone to make the histogram large while keeping the number of events in the cell with the most events high.
i. This final frequency-of-occurrence histogram is normalized by dividing each cell of the 50×50 grid by he number of events in the histogram (i.e. the area of the histogram is one.

What is claim is:
1. An apparatus for rapidly detecting and identifying microscopic particles for quantitative and qualitative measurement comprising:

a) a polarized laser that produces a beam waist;
b) an optical chassis including multiple light detectors, each light detector positioned around and oriented to view, without obscuration, a common region of regard of the laser beam waist;
c) a sample chamber for containing a fluid sample to be analyzed;
d) means for holding the sample chamber in a prescribed orientation with respect to the laser beam waist and in the common region of regard of the light detectors;
e) means for causing the particles in the sample to circulate through the laser beam waist;
f) means for covering the light source and optical chassis to create a dark enclosure;
g) means for converting the light intensity values measured by the detectors into digital values;
h) means for continuously entering the digital values into a computer;
i) means for determining when a particle has entered the light beam at the common region of regard based on the digitized measurements;
j) means for converting the digitized values to calibrated values;
k) means for extracting Event Descriptors from the digitized and calibrated event data;
l) means for calculating Discriminant Function values from the Event Descriptors;
m) means for defining probability histograms that enable the calculation of the probability that a Discriminant Function value calculated from measured values was caused by a specific particle species; and
n) means for identifying the unknown particle based on a threshold.

2. An apparatus as defined in claim 1 and further comprising means for identifying the most effective Discriminant Functions.

3. An apparatus as defined in claim 1 and further comprising means for storing the probability histograms and Discriminant Functions in an Identification Library, one histogram for each particle species that can be identified and each Discriminant Function.

4. An apparatus as defined in claim 1 and further comprising means for retrieving previously stored probability histograms and Discriminant Functions, one probability histogram for each particle species that can be identified with the Identification Library and each Discriminant Function.

5. An apparatus as defined in claim 1 and further comprising means for calculating the probability for each particle species in the library for a given value of a Discriminant Function.

6. An apparatus as defined in claim 1 and further comprising means for combining probabilities for each particle species that can be identified with the Identification Library.

7. An apparatus as defined in claim 1 and further comprising means for identifying the unknown particle based on a threshold.

* * * * *